(12) United States Patent
Ali et al.

(10) Patent No.: US 7,030,164 B2
(45) Date of Patent: Apr. 18, 2006

(54) CRYSTALLINE POLYMORPH OF VENLAFAXINE HYDROCHLORIDE AND METHODS FOR THE PREPARATION THEREOF

(75) Inventors: Kadum Abdul Nabi Ali, Congers, NY (US); Jun Han, Park City, IL (US); Yong Jai Lee, Monroe, NY (US)

(73) Assignee: Wyeth, Madison, NJ (US)

( * ) Notice: Subject to any disclaimer, the term of this patent is extended or adjusted under 35 U.S.C. 154(b) by 472 days.

(21) Appl. No.: 10/308,480

(22) Filed: Dec. 3, 2002

(65) Prior Publication Data

US 2003/0109585 A1 Jun. 12, 2003

Related U.S. Application Data

(60) Provisional application No. 60/335,822, filed on Dec. 5, 2001.

(51) Int. Cl.
*A61K 31/135* (2006.01)
(52) U.S. Cl. ...................... 514/649; 564/336
(58) Field of Classification Search ................ 564/336; 514/649
See application file for complete search history.

(56) References Cited

U.S. PATENT DOCUMENTS

| | | | |
|---|---|---|---|
| 4,761,501 A | | 8/1988 | Husbands et al. |
| 5,506,270 A | | 4/1996 | Upton et al. |
| 5,530,013 A | | 6/1996 | Husbands et al. |
| 5,744,474 A | | 4/1998 | Thor |
| 5,916,923 A | | 6/1999 | Rudolph et al. |
| 6,274,171 B1 | | 8/2001 | Sherman et al. |
| 6,906,087 B1 * | | 6/2005 | Van Der Schaaf et al. . 514/336 |
| 2002/0143211 A1 * | | 10/2002 | Dolitzky et al. ............ 564/316 |
| 2002/0183553 A1 * | | 12/2002 | Dolitzky et al. ............ 564/316 |
| 2003/0105359 A1 * | | 6/2003 | Van Der Schaaf et al. . 564/339 |
| 2003/0114536 A1 * | | 6/2003 | Han et al. .................... 514/649 |
| 2004/0220278 A1 * | | 11/2004 | Dolitzky et al. ............ 514/649 |
| 2005/0049304 A1 * | | 3/2005 | Dolitzky et al. ............ 514/521 |

FOREIGN PATENT DOCUMENTS

| | | |
|---|---|---|
| WO | WO 94/27589 | 12/1994 |
| WO | WO 02/36542 A1 | 5/2002 |
| WO | WO 02/45658 A2 | 6/2002 |
| WO | WO 02/46140 A1 | 6/2002 |

OTHER PUBLICATIONS

Daniel Vega et al., Acta Cryst., 2000, 1009-1010, C56.

* cited by examiner

*Primary Examiner*—Samuel Barts
(74) *Attorney, Agent, or Firm*—Rebecca R. Barrett (57) ABSTRACT

This invention relates to a highly thermally stable novel anhydrous crystalline polymorphic form of venlafaxine hydrochloride, methods for the preparation thereof, and its use.

10 Claims, 5 Drawing Sheets

CRYSTALLINE POLYMORPH OF VENLAFAXINE HYDROCHLORIDE AND METHODS FOR THE PREPARATION THEREOF

This application claims priority from provisional application Ser. No. 60/335,822, filed on Dec. 5, 2001, the entire disclosure of which is hereby incorporated by reference.

1. Field of the Invention

This invention relates to a novel highly thermally stable anhydrous crystalline polymorphic form of venlafaxine hydrochloride, methods for the preparation thereof, and its use.

2. Background of the Invention

Venlafaxine (1-[2-(dimethylamino)-1-(4-methoxyphenyl) ethyl]cyclohexanol) and its therapeutically acceptable salts (collectively referred to as venlafaxine herein) are inhibitors of monoamine neurotransmitter uptake, a mechanism associated with clinical antidepressant activity. This mechanism has also been associated with reproductive function by affecting indirectly the hypothalamic-pituitary-ovarian axis. It is believed that venlafaxine's mechanism of action is related to potent inhibition of the uptake of the monoamine neurotransmitters serotonin and norepinephrine. To a lesser degree, venlafaxine also inhibits dopamine reuptake. However, it has no inhibitory activity on monoamine oxidase.

In contrast to classical tricyclic antidepressant drugs, venlafaxine has virtually no affinity for muscaranic, histaminergic, or adrenergic receptors in vitro. Pharmacologic activity at these receptors is associated with the various anticholinergic, sedative, and cardiovascular effects seen with the tricyclic antidepressant drugs.

Hypothalamic amenorrhea in depressed and non-depressed human females may also be treated with venlafaxine as taught in U.S. Pat. No. 5,506,270.

U.S. Pat. No. 5,530,013 teaches that venlafaxine induces cognition enhancement and treats cognitive impairment in a mammal.

U.S. Pat. No. 5,744,474 discloses that venlafaxine can treat urinary incontinence in humans.

More recently, as discussed in U.S. Pat. No. 5,916,923, venlafaxine has been found to treat, prevent, and control obesity, generalized anxiety disorder, post-traumatic stress disorder, late luteal phase disphoric disorder (premenstrual syndrome), attention deficit disorder (with and without hyperactivity), Gilles de la Tourette syndrome, bulimia nervosa, and Shy Drager Syndrome in mammals (e.g., humans).

Figure 2:
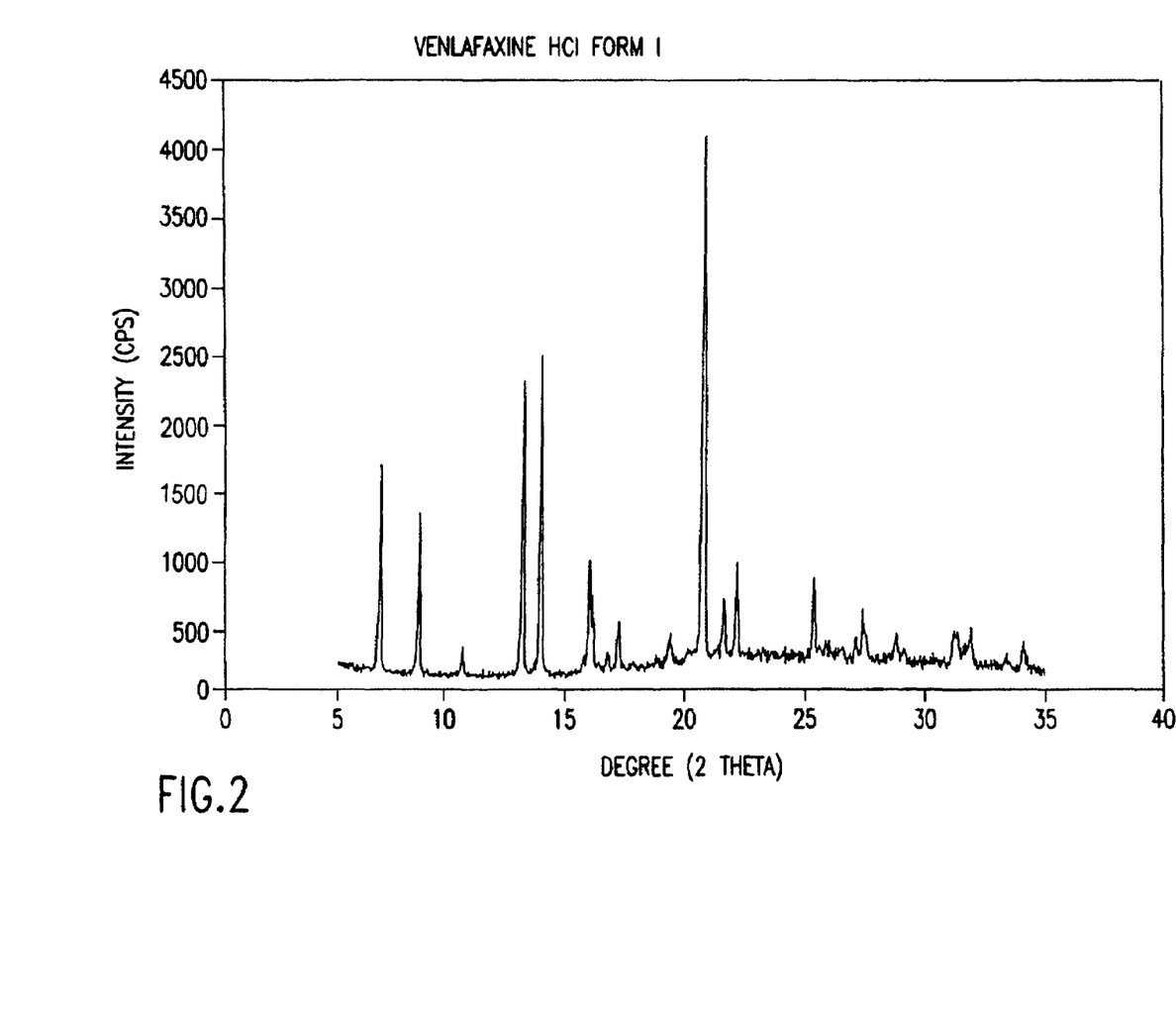
FIG. 2 is a characteristic XRPD pattern of Form I of venlafaxine hydrochloride.
Figure 3:
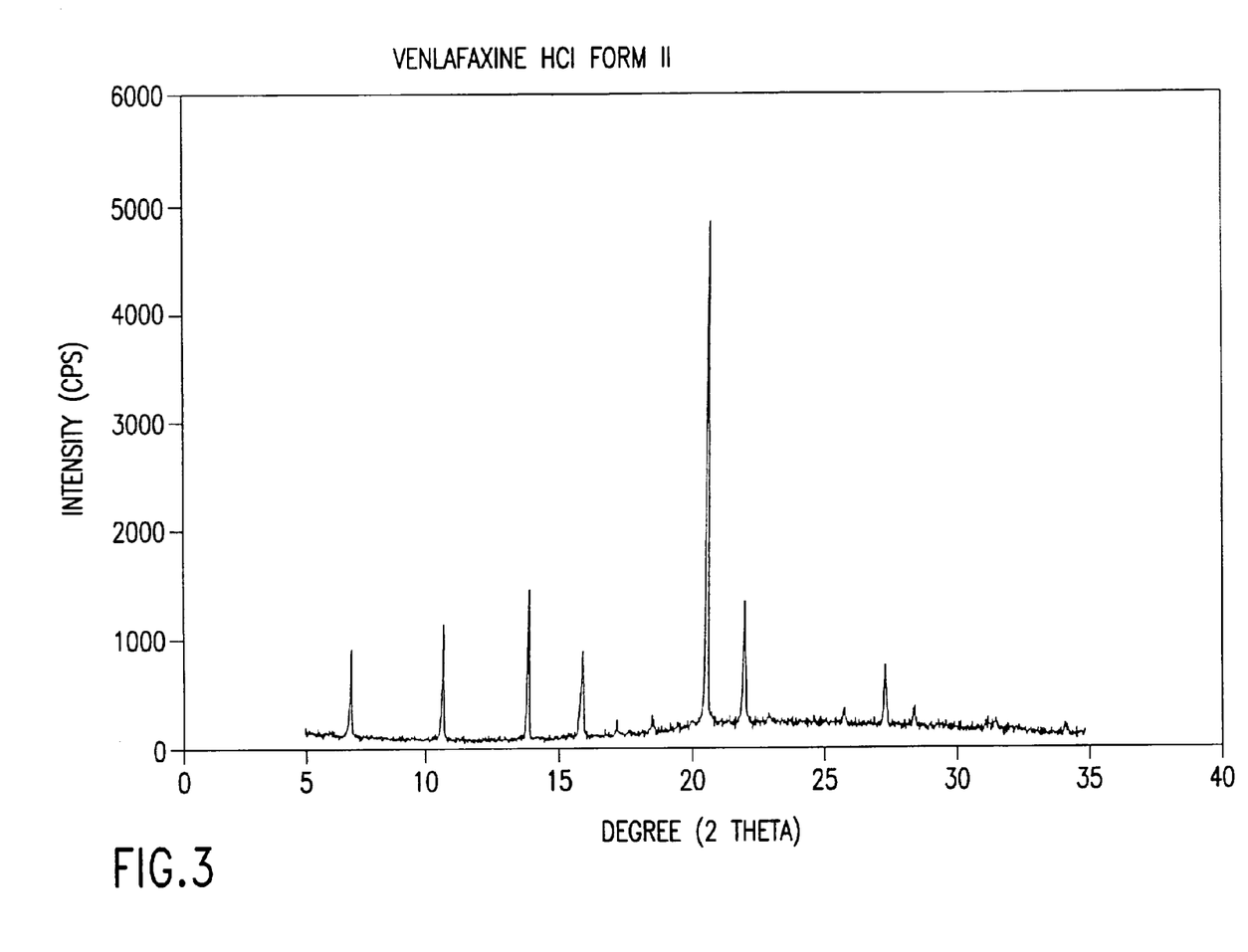
FIG. 3 is a characteristic XRPD pattern of Form II of venlafaxine hydrochloride.

Extended release formulations of venlafaxine are disclosed in U.S. Pat. No. 6,274,171 and International Patent Publication No. WO 94/27589. As discussed in U.S. Pat. No. 6,274,171, venlafaxine hydrochloride is known to exist in two polymorphic forms, Forms I and II. Characteristic X-ray powder diffraction patterns for Forms I and II are shown in FIGS. 2 and 3, respectively.

SUMMARY OF THE INVENTION

The present invention provides a novel anhydrous crystalline polymorph of venlafaxine hydrochloride. This crystalline polymorph is more thermally stable than known forms of venlafaxine hydrochloride. While forms I and II of venlafaxine hydrochloride have melting points of 209 and 211° C. ($\Delta H$=125.8 and 130.3 J/g), respectively, the melting point of the crystalline polymorph of the present invention is about 219° C. ($\Delta H$=116 J/g). Because of this stability, a mixture of various polymorphs of venlafaxine hydrochloride can be formed into a pure form of this new polymorph. Furthermore, residual solvents used in the preparation of this new polymorph or the precursor venlafaxine hydrochloride can be easily removed.

The crystalline polymorph of the present invention exhibits characteristic XRPD peaks (expressed in degrees $2\theta$) at about 5.67, 7.28, 9.14, 9.67, 10.77, 11.31, 14.01, 14.54, 14.85, 15.48, 15.81, 16.17, 16.94, 17.68, 18.02, 18.48, 19.29, 19.69, 20.46, 20.74, 21.86, 22.33, 22.67, 22.95, 23.17, 24.06, 24.61, 25.13, 26.62, 26.97, 27.64, 28.25, 29.01, 29.96, 31.01, 31.61, 32.75, 34.54, 35.50, 35.95 and 36.91.

The crystalline polymorph of the present invention can be administered to a mammal to treat depression (including, but not limited to, major depressive disorder, bipolar disorder, and dysthymia), fibromyalgia, anxiety, panic disorder, agorophobia, post traumatic stress disorder, premenstrual dysphoric disorder (premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction (including premature ejaculation), borderline personality disorder, chronic fatigue syndrome, urinary incontinence, pain (including, but not limited to, migraine, chronic back pain, phantom limb pain, central pain, neuropathic pain such as diabetic neuropathy, and postherpetic neuropathy), Shy Drager Syndrome, or Raynaud's syndrome. The crystalline polymorph can also be administered to prevent relapse or recurrence of depression, to induce cognitive enhancement, to treat cognitive impairment, and in regimens for cessation of smoking or other tobacco uses. Additionally, the crystalline polymorph can be administered to treat hypothalamic amenorrhea in depressed and non-depressed human females. These methods involve administering to a mammal (e.g., a human) in need thereof an effective amount of the crystalline polymorph of the present invention or a mixture of venlafaxine polymorphs that contains the crystalline polymorph of the present invention. Preferably, the venlafaxine is administered orally.

Another embodiment is a pharmaceutical composition comprising the crystalline polymorph of the present invention and, optionally, a pharmaceutically acceptable carrier or diluent. Typically, the pharmaceutical composition comprises an amount of the crystalline polymorph effective to treat depression or any of the aforementioned indications in an animal, such as a mammal (e.g. human). According to one preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of the crystalline polymorph of the present invention, based upon 100% total weight of venlafaxine hydrochloride in the pharmaceutical composition. According to another preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of the crystalline polymorph of the present invention, based upon 100% total weight of venlafaxine hydrochloride in the pharmaceutical composition.

The pharmaceutical composition may be incorporated into a dosage form, such as a tablet or capsule.

The crystalline polymorph of the present invention can be prepared by heating venlafaxine hydrochloride of form I or II or mixtures thereof to a temperature of at least about 197° C. and more preferably at least about 200° C. According to one embodiment, the venlafaxine hydrochloride is heated to about 200° C. Generally, the venlafaxine hydrochloride is heated for at least about 60 minutes and more preferably for at least about 150 minutes. The crystals formed may be recovered by any method known in the art.

Another embodiment is a method of preparing a substantially pure crystalline polymorphic form of venlafaxine hydrochloride. The method includes obtaining the venlafaxine hydrochloride crystalline polymorph of the present invention in substantially pure form and then converting the substantially pure venlafaxine hydrochloride into another polymorphic form, such as form I. The substantially pure venlafaxine hydrochloride product can be incorporated into pharmaceutical compositions and dosage forms as known in the art.

DETAILED DESCRIPTION OF THE INVENTION

The term "about" generally means within 10%, preferably within 5%, and more preferably within 1% of a given value or range. With regard to a given value or range in degrees 2θ from XRPD patterns, the term "about" generally means within 0.2° 2θ and preferably within 0.1°, 0.05°, or 0.01° 2θ of the given value or range. Alternatively, the term "about" means within an acceptable standard error of the mean, when considered by one of ordinary skill in the art.

The term "treat" as used herein refers to preventing, ameliorating, controlling, or curing the desired symptoms or disorders.

The term "venlafaxine hydrochloride" as used herein refers to racemic mixtures of R and S-venlafaxine and their optically pure enantiomers. The crystalline polymorph of the present invention may be R, S, or a racemic mixture of R and S-venlafaxine hydrochloride.

Figure 1:
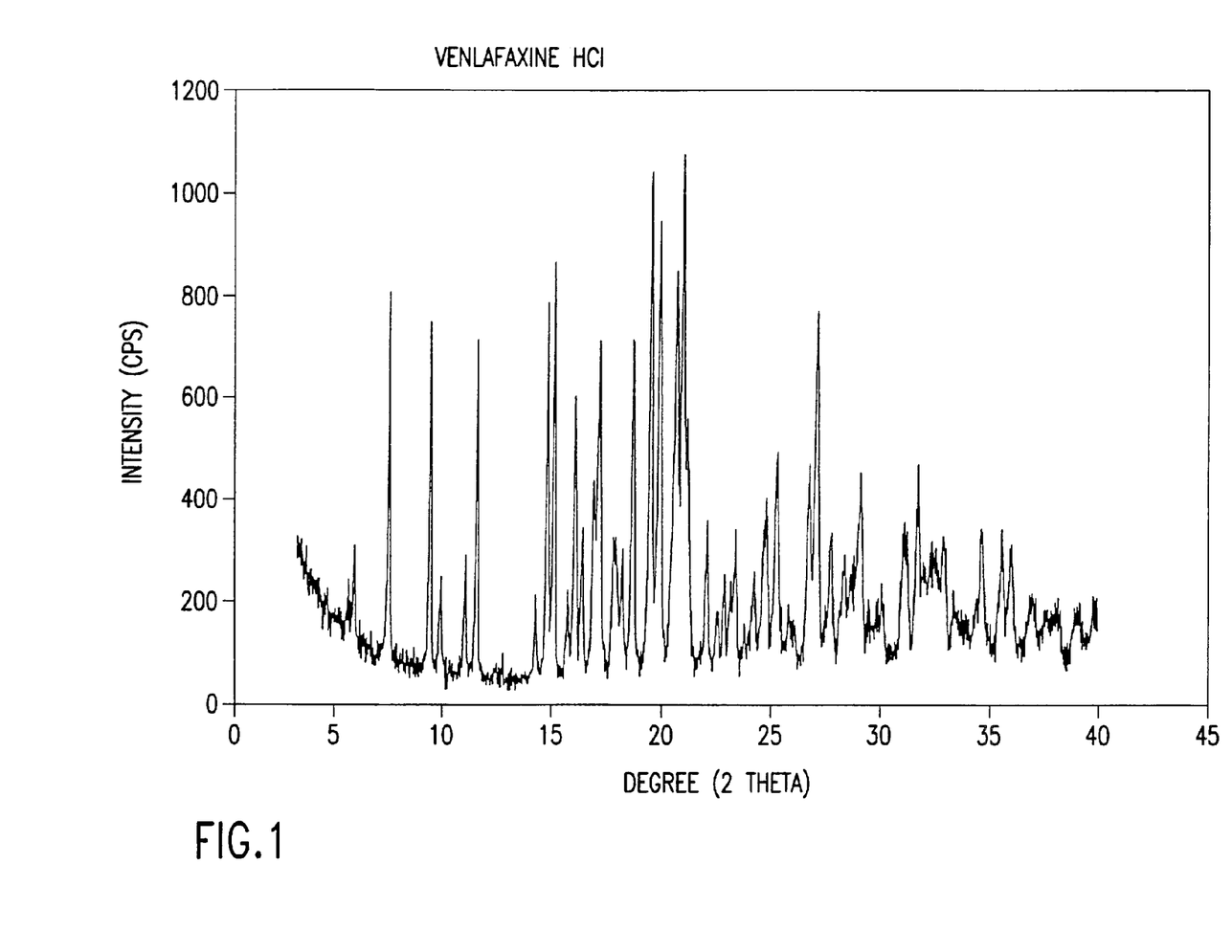
FIG. 1 is a characteristic X-ray Powder Diffraction (XRPD) pattern of the anhydrous venlafaxine hydrochloride crystalline polymorph of the present invention.

The crystalline polymorph has an XRPD pattern substantially identical to that shown in FIG. 1. Peak locations and intensities for the XRPD pattern in FIG. 1 are provided in Table 1 below.

TABLE I

Characteristic XRPD Peaks (expressed in degrees 2θ) D-spacing in Angstrom (Å) and Intensities of Diffraction Lines in CPS for the Polymorphic Form of Venlafaxine Hydrochloride

| Degrees 2θ | d (Å) | I (Counts per Second (CPS) |
|---|---|---|
| 5.67 | 15.57 | 309.09 |
| 7.28 | 12.14 | 828.73 |
| 9.14 | 9.67 | 766.93 |
| 9.67 | 9.14 | 262.26 |
| 10.77 | 8.21 | 303.39 |
| 11.31 | 7.82 | 728.55 |
| 14.01 | 6.31 | 224.07 |
| 14.54 | 6.09 | 807.87 |
| 14.85 | 5.96 | 887.19 |
| 15.48 | 5.72 | 830.41 |
| 15.81 | 5.60 | 617.50 |
| 16.17 | 5.48 | 357.33 |
| 16.94 | 5.23 | 728.55 |
| 17.68 | 5.01 | 338.29 |
| 18.02 | 4.92 | 312.91 |
| 18.48 | 4.80 | 753.93 |
| 19.29 | 4.60 | 1069.82 |
| 19.69 | 4.50 | 963.51 |
| 20.46 | 4.34 | 866.61 |
| 20.74 | 4.28 | 1084.34 |
| 21.86 | 4.06 | 365.61 |
| 22.33 | 3.98 | 187.75 |
| 22.67 | 3.92 | 259.14 |
| 22.95 | 3.87 | 240.39 |
| 23.17 | 3.84 | 343.83 |
| 24.06 | 3.70 | 264.69 |
| 24.61 | 3.62 | 403.19 |
| 25.13 | 3.54 | 498.24 |
| 26.62 | 3.35 | 479.23 |
| 26.97 | 3.30 | 783.01 |
| 27.64 | 3.23 | 338.01 |
| 28.25 | 3.16 | 294.56 |
| 29.01 | 3.08 | 452.07 |
| 29.96 | 2.98 | 237.53 |
| 31.01 | 2.88 | 348.88 |
| 31.61 | 2.83 | 478.42 |
| 32.75 | 2.73 | 332.38 |
| 34.54 | 2.60 | 347.78 |
| 35.50 | 2.53 | 338.55 |
| 35.95 | 2.50 | 315.92 |
| 36.91 | 2.43 | 221.30 |

In particular, the peaks (expressed in degrees 2θ) at about 5.67, 7.28, 9.14, 9.67, 10.77, 14.01, 14.54, 16.17, 19.69, and 20.74 are unique to this crystalline polymorph. The crystalline polymorph also has a melting endotherm, according to differential scanning calorimetry, at 219° C.

The crystalline polymorph of the present invention is useful for treating, preventing, or controlling depression and the aforementioned indications. The appropriate dosage amounts for an animal can be determined by methods known in the art. Generally, a therapeutic effective amount for the desired purpose is administered. The dosage of the crystalline polymorph of venlafaxine hydrochloride disclosed herein is generally from about 75 to about 300 mg per day.

The crystalline polymorph can be formulated into a pharmaceutical composition. Preferably, the pharmaceutical composition comprises an amount of the crystalline polymorph of venlafaxine hydrochloride effective to treat the desired indication in an animal, such as a human. According to one preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of the crystalline polymorph of venlafaxine hydrochloride, based upon 100% total weight of venlafaxine hydrochloride in the pharmaceutical composition. According to another embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of the crystalline polymorph of venlafaxine hydrochloride, based upon 100% total weight of crystalline venlafaxine hydrochloride in the pharmaceutical composition.

The pharmaceutical composition can also be substantially free or completely free of other crystalline polymorphs of venlafaxine hydrochloride, such as Forms I and II. The terms "substantially free" and "substantially pure" include those pharmaceutical compositions that contain less than 0.01, 0.1, 0.2, 0.3, 0.4, 0.5, 1 or 2% by weight of other crystalline polymorphs, such as Form I or II or both, based upon the total weight of pharmaceutical composition (or alternatively based upon on the total weight of venlafaxine hydrochloride in the pharmaceutical composition).

According to one embodiment, the pharmaceutical composition contains from about 25 to about 350 mg of the crystalline polymorph of venlafaxine hydrochloride. More preferably, pharmaceutical compositions of the present invention contain 75 mg, 150 mg or 225 mg of the crystalline polymorph of venlafaxine hydrochloride.

The pharmaceutical composition may also include one or more pharmaceutically acceptable carriers or diluents and excipients. The term "excipient" includes, but is not limited to, those materials that are acceptable for use in pharmaceutical formulations, and are added to the formulation to promote the stability and viability of the formulation, such as binders, bulking agents, clarifying agents, buffering agents, wetting agents, lubricants, sweeteners, and flavoring agents. Suitable excipients include, but are not limited to, cellulose, ethyl cellulose, gelatin, hydroxypropyl methylcellulose, iron oxide, titanium dioxide, lactose, magnesium stearate, and sodium starch glycolate. Suitable pharmaceutically acceptable carriers, diluents, and excipients also include those described in Remington's, The Science and Practice of Pharmacy, (Gennaro, A.R., ed., 19$^{th}$ edition, 1995, Mack Pub. Co.) which is herein incorporated by reference. The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g. a human).

According to one preferred embodiment, the pharmaceutical composition is an extended release formulation, such as that described in U.S. Pat. No. 6,274,171, which is herein incorporated by reference. For example, an extended release formulation may comprise spheroids comprised of the crystalline polymorph of the present invention, microcrystalline cellulose, and, optionally, hydroxypropyl-methylcellulose. The spheroids are preferably coated with a film coating composition comprised of ethyl cellulose and hydroxypropylmethylcellulose.

The pharmaceutical composition may be a dosage form, such as a liquid (e.g., elixirs and suspensions), capsule, pill, or tablet. The pharmaceutical compositions and the crystalline polymorph of venlafaxine hydrochloride may be administered to animals, including, but not limited to, mammals (e.g. humans), orally, intravenously, intramuscularly, parenterally intraperitoneally, subdermally, buccally, subcutaneously, transdermally, topically, rectally, vaginally, or intranasally. Preferably, the composition is administered orally.

The crystalline polymorph of the present invention can be prepared by heating venlafaxine hydrochloride of form I or II or mixtures thereof to at least about 197° C. and more preferably at least about 200° C. According to one embodiment, the venlafaxine hydrochloride is heated to about 200° C. Generally, the venlafaxine hydrochloride is heated for a time sufficient to form the crystalline polymorph of the present invention. Preferably, the venlafaxine hydrochloride precursor is heated for at least about 60 minutes and more preferably for at least about 150 minutes. The crystalline polymorph may be prepared in substantially pure form by heating the venlafaxine hydrochloride precursor for a sufficient amount of time.

Venlafaxine hydrochloride may be prepared by any method known in the art including, but not limited to, the methods described in U.S. Pat. Nos. 4,535,186 and 4,761,501 and International Patent Publication Nos. WO 00/32555, WO 00/32556, and WO 01/07397, all of which are hereby incorporated by reference.

The crystals formed may be recovered by any method known in the art, such as filtration, centrifugation, or with a Buchner style filter, Rosenmund filter, or plates and frame press. Typically, the crystals are recovered as solids.

The crystalline polymorph can be converted into Form I by recrystallizing it in ethyl acetate in ethanol (e.g., 80% ethyl acetate in ethanol).

As discussed above, substantially pure forms of the crystalline polymorph can be prepared such as by heating one or more forms of venlafaxine hydrochloride to about 200° C. for a sufficient time. The substantially pure crystalline polymorph can be used to prepare other substantially pure crystalline polymorphic forms of venlafaxine hydrochloride, such as form I, by the methods described above. The substantially pure venlafaxine hydrochloride product can be incorporated into pharmaceutical compositions and dosage forms as known in the art.

EXAMPLES

The following examples are illustrative and are not meant to limit the scope of the claimed invention. The venlafaxine hydrochloride which is used as a raw material in the example below can be prepared by any method known in the art.

Example 1

Preparation of Anhydrous Venlafaxine Hydrochloride

About 100 mg of venlafaxine hydrochloride of Form II was put in a glass vial, flushed with nitrogen gas and then sealed by heat. The sealed vial was put in an oil bath at about 200° C. (197° C. to 200° C.) for 1 hour or until the shape of the crystals changed to form cream-white crystals.

Example 2

Preparation of Anhydrous Venlafaxine Hydrochloride

The procedure in Example 1 was repeated with 500 mg of venlafaxine hydrochloride of Form II, except the vial was left in the oil bath for 2.5 hours instead of 1 hour.

Example 3

Preparation of Anhydrous Venlafaxine Hydrochloride

The procedure in Example 1 was repeated, except an aluminum vial was used instead of a glass vial.

Example 4

X-Ray Powder Diffraction (XRPD)

XRPD was performed on the crystalline polymorph of venlafaxine hydrochloride of the present invention under dry conditions with a Scintag X2 X-Ray Diffraction System Model 00-A02, available from Thermo ARL of Ecublens, Switzerland. The XRPD instrument had the following parameters:

| | |
|---|---|
| Scan Type: | Normal |
| Start Angle: | 3 degrees |
| Stop Angle: | 40 degrees |
| Number of Points: | 1851 points |
| Step Size: | 0.02 degrees |
| Datafile Resolution: | 1600 |
| Scan Rate: | 0.04 |
| Scan Mode: | Step |
| Wavelength: | 1.540562 |
| Diffraction Optics: | |
| Detector: | |
| Type: | Fixed Slits |
| X2 Configuration: | No |
| Tube: | |
| Type: | Fixed Slits |
| X2 Configuration: | No |

The results are shown in FIG. 1.

This procedure was repeated for Forms I and II of venlafaxine hydrochloride.

The results for Forms I and II are shown in FIGS. 2 and 3, respectively.

Example 5

Intrinsic Dissolution Rate

The intrinsic dissolution rates of Form II and the crystalline polymorph of the present invention were determined as follows. Pellets of venlafaxine hydrochloride were prepared by compressing 100 mg of each material in a die (Wood's apparatus) at 1000 psi for 1 minute with a Carver press. The pellets produced were then fitted into a dissolution apparatus (Vankel 7010 equipped with a Cary 300 Ultraviolet/Visible Spectrophotometer) which resulted in a single exposed surface area of 0.5 $cm^2$. The dissolution rate in 900 mL of water was determined by USP 23 (1995), section 711, page 1791 (Dissolution, apparatus 2), with a rotation speed of 100 rpm at 37° C. The dissolution media was circulated through a 1.0 cm path microflow cell at a flow rate of 10 mL/minute. Ultraviolet absorbance was recorded at 220 nm.

Both Form II and the crystalline polymorph of the present invention exhibited dissolution rates of 24.7 $mg/cm^2$-minute.

Example 6

Differential Scanning Calorimetry (DSC)

DSC measurements on the anhydrous venlafaxine hydrochloride crystalline polymorph of the present invention were carried out in a sealed pan at a scan rate of 10° C./minute from 25° C. to 240° C. under a nitrogen purge with a Pyris I DSC available from Perkin-Elmer of Shelton, Conn. The DSC scan is shown in FIG. 4.

Figure 4:
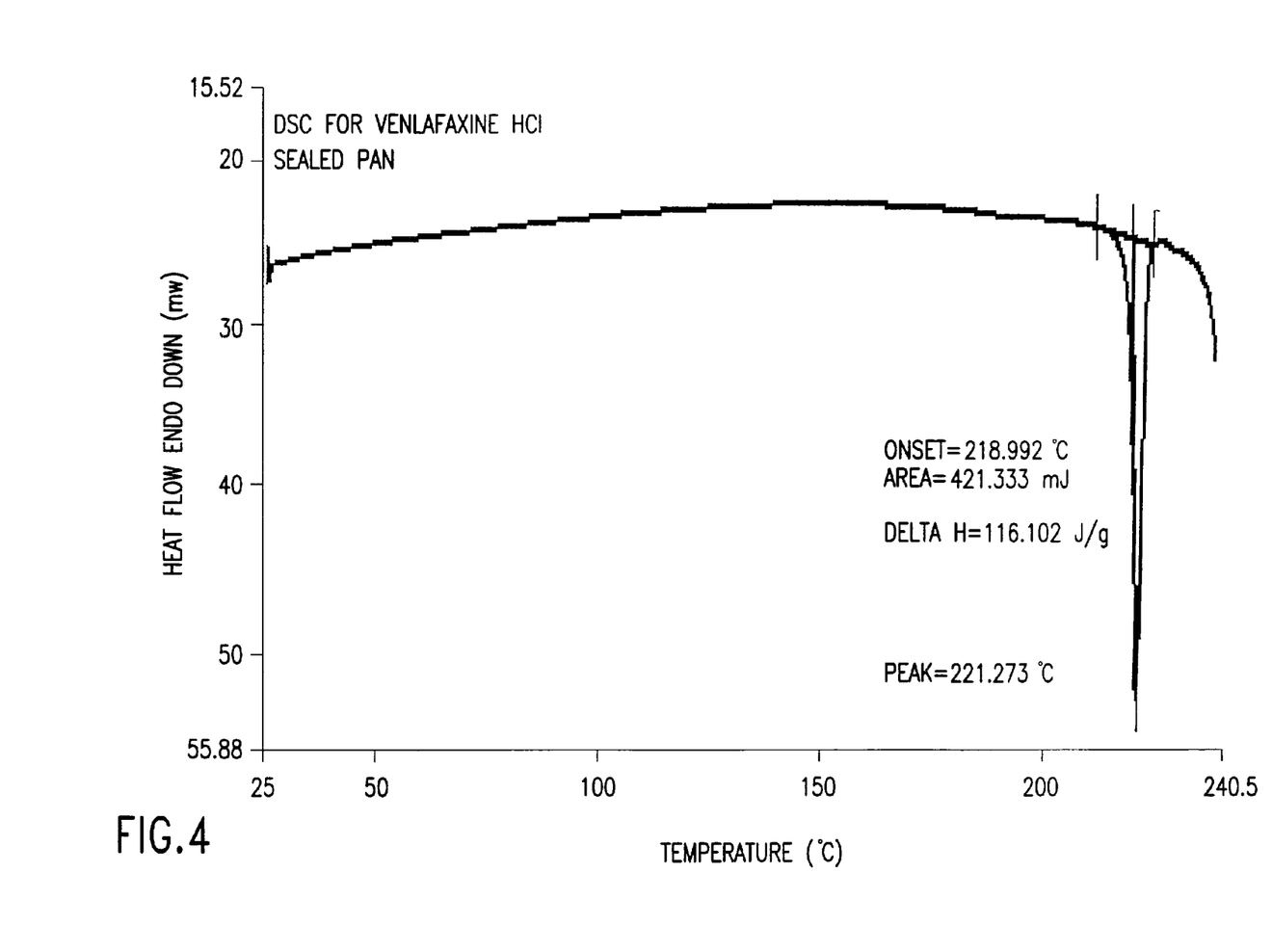
FIG. 4 is a differential scanning calorimetry (DSC) scan of the anhydrous venlafaxine hydrochloride crystalline polymorph of the present invention carried out in a sealed pan at a scan rate of 10° C./minute from 25 to 240° C. under a nitrogen purge.

FIG. 4 shows one endotherm at 221° C. (heat of fusion is 116 J/g), which was the melting of the anhydrous venlafaxine hydrochloride. The onset melting temperature for the venlafaxine hydrochloride was 219° C.

Example 7

Thermogravimetric Analysis (TGA)

Figure 5:
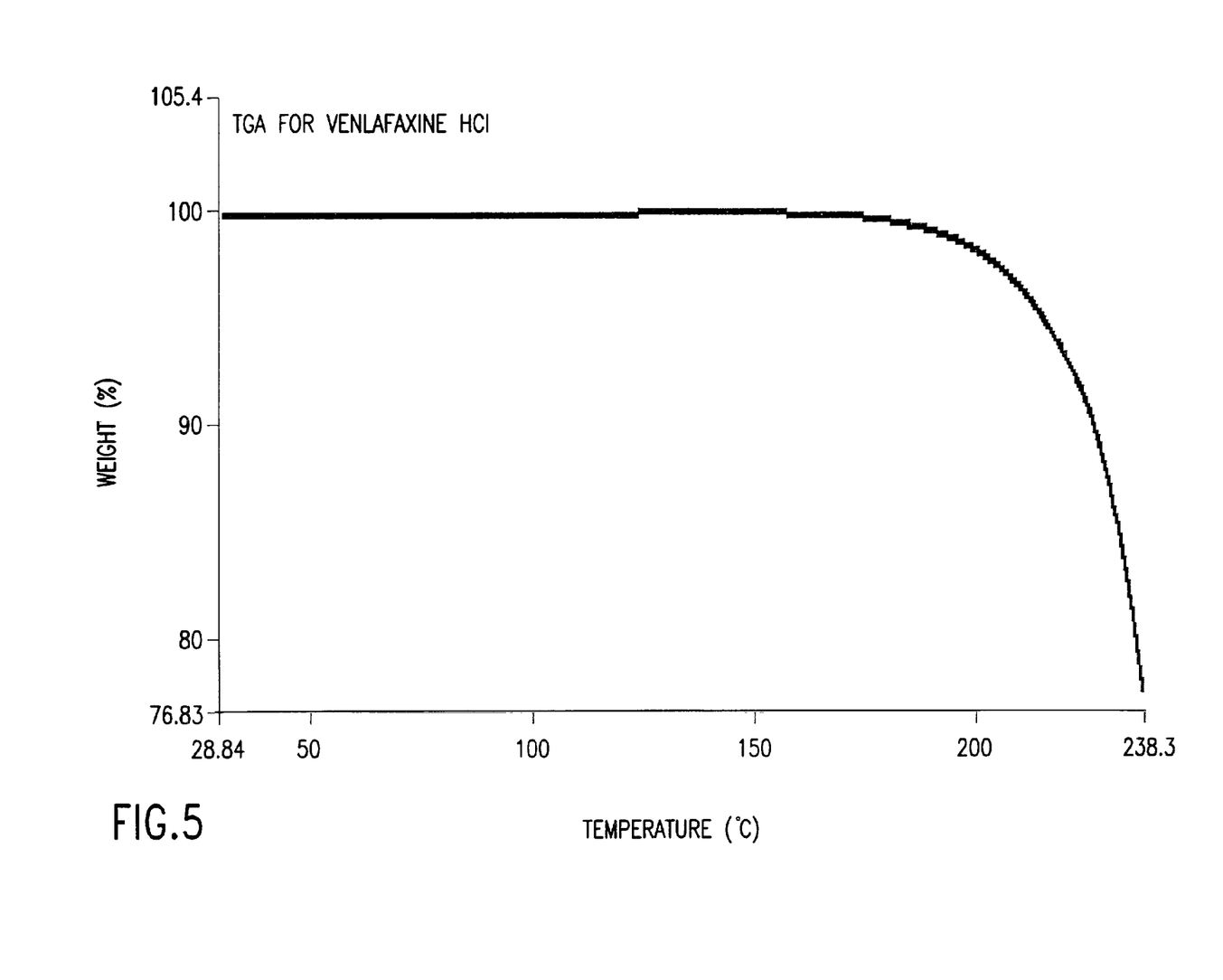
FIG. 5 is a thermogravimetric analysis (TGA) of the anhydrous crystalline polymorph of the present invention heated from 28 to 238° C. at a scan rate of 10° C./minute under a nitrogen purge.

A sample of the venlafaxine hydrochloride crystalline polymorph of the present invention was heated from 28 to 238° C. at a scan rate of 10° C./minute in a Pyris I TGA, available from Perkin-Elmer of Shelton, Conn., under a nitrogen purge. The results are shown in FIG. 5. The sample lost little weight until it was heated near the melting point of venlafaxine hydrochloride.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that values are approximate, and are provided for description.

Patents, patent applications, publications, procedures, and the like are cited throughout this application, the disclosures of which are incorporated herein by reference in their entireties. To the extent that a conflict may exist between the specification and a reference, the language of the disclosure made herein controls.

What is claimed is:

1. Venlafaxine hydrochloride having an X-ray powder diffraction pattern substantially the same as that shown in FIG. 1.

2. The venlafaxine hydrochloride of claim 1, wherein the venlafaxine hydrochloride is anhydrous.

3. The venlafaxine hydrochloride of claim 1, wherein the melting point of the venlafaxine hydrochloride is about 219° C.

4. Substantially pure venlafaxine hydrochloride having an X-ray powder diffraction pattern substantially the same as that shown in FIG. 1.

5. A crystalline polymorph of venlafaxine hydrochloride exhibiting an X-ray powder diffraction pattern having characteristic peaks expressed in degrees 2θ at about 5.67, 7.28, 9.14, 9.67, 10.77, 11.31, 14.01, 14.54, 14.85, 15.48, 15.81, 16.17, 16.94, 17.68, 18.02, 18.48, 19.29, 19.69, 20.46, 20.74, 21.86, 22.33, 22.67, 22.95, 23.17, 24.06, 24.61, 25.13, 26.62, 26.97, 27.64, 28.25, 29.01, 29.96, 31.01, 31.61, 32.75, 34.54, 35.50, 35.95 and 36.91.

6. A crystalline polymorph of venlafaxine hydrochloride exhibiting an X-ray powder diffraction pattern having characteristic peaks expressed in degrees 2θ at about 5.67, 7.28, 9.14, 9.67, 10.77, 14.01, 14.54, 16.17, 19.69, and 20.74.

7. A pharmaceutical composition comprising a therapeutically effective amount of the venlafaxine hydrochloride of claim 1 and a pharmaceutically acceptable carrier or diluent.

8. The pharmaceutical composition of claim 7, wherein the venlafaxine hydrochloride is substantially pure.

9. The pharmaceutical composition of claim 7, wherein the pharmaceutical composition contains less than 1% by weight of crystalline polymorphs of venlafaxine hydrochloride having an X-ray powder diffraction pattern substantially the same as that shown in FIG. 1, based upon 100% total weight of venlafaxine hydrochloride in the pharmaceutical composition.

10. The pharmaceutical composition of claim 7, wherein the composition comprises a plurality of spheroids comprising the venlafaxine hydrochloride.

* * * * *